United States Patent [19]

Mitchell et al.

[11] Patent Number: 5,036,837
[45] Date of Patent: Aug. 6, 1991

[54] DYNAMIC EXTENSION SPLINT

[75] Inventors: Andrew Mitchell, Kennett Square, Pa.; William L. Muir, North East, Md.; Richard DeLorenzo, Wilmington, Del.

[73] Assignee: Bio-Tec, Inc., Wilmington, Del.

[21] Appl. No.: 477,460

[22] Filed: Feb. 9, 1990

[51] Int. Cl.$^5$ ............................................. A61F 5/04
[52] U.S. Cl. .................................. 128/84 R; 128/88
[58] Field of Search ............... 128/84 R, 84 C, 80 R, 128/80 A, 80 C, 80 F, 80 G, 88, 89 R, 87 A, 87 R

[56] References Cited

U.S. PATENT DOCUMENTS

| | | | |
|---|---|---|---|
| 1,847,823 | 1/1932 | Dresser | 128/88 |
| 4,252,111 | 2/1981 | Chao | 128/80 F |
| 4,397,308 | 8/1983 | Hepburn | 128/88 |
| 4,485,808 | 12/1984 | Hepburn | 128/87 R |
| 4,489,718 | 12/1984 | Martin | 128/80 C |
| 4,493,316 | 1/1985 | Reed | 128/88 |
| 4,508,111 | 4/1985 | Hepburn | 128/87 R |
| 4,538,600 | 9/1985 | Hepburn | 128/88 |
| 4,633,867 | 1/1987 | Kausek | 128/88 |
| 4,657,000 | 4/1987 | Hepburn | 128/88 |
| 4,726,361 | 2/1988 | Farley | 128/88 |
| 4,738,252 | 4/1988 | Friddle | 128/80 C |
| 4,817,588 | 4/1989 | Bledsoe | 128/80 C |
| 4,844,057 | 7/1989 | Hoy | 128/88 |
| 4,865,024 | 9/1989 | Hensley | 128/80 C |

Primary Examiner—Robert A. Hafer
Assistant Examiner—Michael Brown
Attorney, Agent, or Firm—Sixbey, Friedman, Leedom & Ferguson

[57] ABSTRACT

A dynamic extension splint is provided which has a pair of elongated strut assemblies which each include a pivotal joint. Each strut assembly is removably supported on one side of a strut support unit which operates to mount the strut assemblies on a body member in alignment with a body joint. A strut assembly includes first and second elongated strut members which are flat units which extend from a pivotal joint. This joint connects one end of the first and second strut members for pivotal movement about one or more pivot axes, and a bias unit mounted at the joint opposes pivotal movement of the strut members in one direction and aids such pivotal movement in a second opposite direction. The bias of this bias unit is adjustable by a bias adjustment mechanism also located at the pivotal joint.

34 Claims, 3 Drawing Sheets

DYNAMIC EXTENSION SPLINT

FIELD OF THE INVENTION

The present invention relates to splint assemblies generally, and more particularly to a dynamic extension splint adapted to exert an adjustable force or tension at a body joint.

BACKGROUND OF THE INVENTION

In recent years, dramatic advances have been made in the development of lightweight, compact mechanisms for correcting common and debilitating injuries to body joints such as fingers, wrists, knees, elbows and the like. Perhaps the greatest advances have been made in the design of orthotic brace units which counteract instabilities in a joint by reinforcing the joint as a whole to prevent unwanted motion. Such orthotic devices are typically formed with a mechanical joint supported by a pair of bracing members. The mechanical joint is defined by a pair of side bars, each of which has a hinge-like pivoting joint in its middle with the top and bottom ends of the side bars being connected to bracing members which fit around a body portion above and below the joint to be supported. These devices operate generally by confining the movement of the joint as it bends so that unwanted motions are eliminated or at least minimized. The most commonly known orthoses are orthotic knee braces of the type commonly used by athletes who have suffered injuries to either the ligaments that interconnect the lower femur and upper tibia, or to the bones themselves, which result in knee instabilities.

Joint instability is not the only debilitating condition of a body joint which requires correction. The operation of a body joint may be impaired in a manner which inhibits the operation of the joint in accomplishing extension or flexion. For example, a flexion contracture prevents full extension of the joint, while an extension contracture prevents the joint from being bent or flexed to the full extent. Obviously, the treatment of a flexion contracture or an extension contracture requires more than the mere support against instability provided by many conventional orthotic devices.

To treat flexion and extension contractures, spring-biased splint units have been developed to provide a force across a body joint. These splint devices provide tension which operates in opposition to a flexion or extension contracture and thereby not only provide support in instances where muscular weakness exists, but also enhance rehabilitation. One type of known adjustable spring-loaded splint includes a pair of lower struts and a pair of upper struts of tubular configuration which are pivotally interconnected. Spring biasing units mounted within the tubular struts are adapted to apply an adjustable force at the pivot point which tends to align the two pivoted struts. Such an adjustable splint mechanism is illustrated by U.S. Pat. Nos. 4,397,308, 4,485,808, 4,508,111, 4,538,600 and 4,657,000 to George R. Hepburn.

Although known adjustable splints operate effectively to apply tension across a joint, they are relatively heavy and bulky and consequently impede to some extent free activity at the affected joint. The heavy tubular strut assemblies used in prior art splints are generally not coextensive from the connecting pivot point, and thus may be brought into only parallel rather than axially aligned relationship. It is impossible to contour these heavy struts to conform to the limb of a user, and the degree of pivotal movement permitted by such splints is generally much less than 180°.

Finally, with known prior art adjustable splints, the bias adjustment mechanism for the splint is difficult to reach, and the degree of adjustment is often difficult to ascertain. Accurate adjustment of the bias for such prior art units with the splint in place is not easily accomplished, and the bias structure employed does not facilitate the provision of a polycentric joint structure of the type better suited to the motion of certain joints, such as the knee.

DISCLOSURE OF THE INVENTION

It is a primary object of the present invention to provide a novel and improved dynamic extension splint for the treatment of joint contractures which is easily applied to a body member in the area of the joint to be treated and which is both compact and lightweight.

Another object of the present invention is to provide a novel and improved dynamic extension splint having opposed strut assemblies which incorporate flat strut members adapted to be contoured in place to conform to a body member. This permits customization of the splint for greater comfort.

A further object of the present invention is to provide a novel and improved dynamic extension splint having opposed strut assemblies which may be easily removed from a strut assembly support unit. Each strut assembly includes two elongated strut members which slide into pockets on either side of the joint to be treated.

Yet another object of the present invention is to provide a novel and improved dynamic extension splint which provides a full range of motion for a joint under treatment. The splint incorporates strut members which pivot at a mechanical joint through 180°. Tension is applied to the strut members by a clock spring type of biasing unit mounted at the mechanical joint, and the spring tension is adjustable by means of a bias adjustment mechanism which is also located at the mechanical joint. Thus, the tension applying spring and the bias adjustment are both located entirely at the mechanical joint for the splint.

A further object of the present invention is to provide a novel and improved dynamic extension splint having a polycentric joint mechanism which is adapted to provide a full 180° range of motion. Elongated strut members are mounted on the polycentric joint for pivotal motion about two spaced parallel pivot axes. Each strut member is biased by a separate spring, and the bias of plural springs is simultaneously adjusted by a bias adjustment mechanism. An indicator at the mechanical joint provides an indication of the degree of bias which is set into the springs.

A still further object of the present invention is to provide a dynamic extension splint having an adjustable spring mechanism which is reversible to provide either flexion or extension resistance.

These, and other objects of the present invention are accomplished by providing an adjustable splint having a pair of elongated strut assemblies which each incorporate a pivotal joint between the ends thereof. These strut assemblies are supported on opposite sides of a body joint by a strut support unit which is mountable on a body member and which locates the pivotal joint in alignment with a body joint while providing compression and heat to the body member in the area of the body joint. Each strut assembly includes a first elongated strut member and a second elongated strut member which extend from the pivotal joint. The elongated strut members of each strut assembly are flat units which may be contoured to match the contour of the body member upon which the splint is mounted. The pivotal joint operates to connect one end of the first and second strut members for pivotal movement about a pivot axis between a first extended position where the elongated strut members extend outwardly from opposite sides of the pivotal joint and a second closed position where the first and second strut members extend outwardly in close proximity from the same side of the pivotal joint. A bias unit is provided at the pivotal joint to oppose pivotal movement of the strut members in a first direction and to aid such pivotal movement in a second opposite direction. The bias of this bias unit is adjusted by a bias adjustment mechanism also located at the pivotal joint, while the range of motion provided by the joint can be altered by spring loaded pins which operate as stops for the strut members.

DESCRIPTION OF THE PREFERRED EMBODIMENTS

Referring now to FIGS. 1-5, the dynamic extension splint of the present invention indicated generally at 10 includes a suspension sleeve 12 formed from neoprene foam or similar material having some elasticity. The suspension sleeve is adapted to fit snugly around a limb or other body member in the area of a joint and operates to position a mechanical joint assembly 14 in alignment with a body joint. The compression and heat provided by the suspension sleeve to a body member in the area of an affected body joint helps to alleviate contracture.

Figure 4:
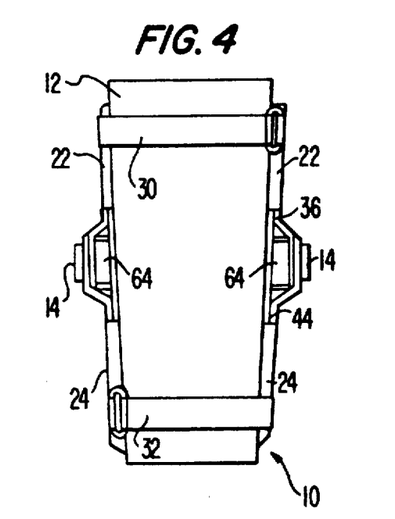
FIG. 4 is a view in front elevation of the strut assembly of FIG. 1.

A pair of mechanical joint assemblies 14 are mounted upon opposite sides of the suspension sleeve 12 as illustrated in FIG. 4, and each mechanical joint assembly includes first and second strut members 16 and 18 which extend outwardly from a mechanical joint or hinge structure 20. The strut members 16 and 18 are removably received in open ended, spaced pockets 22 and 24, respectively, and a pair of such pockets are secured to each of two opposite sides of the suspension sleeve 12. These pockets may be formed of leather or similar material, and operate to facilitate removal of a mechanical joint assembly 14 therefrom. When the mechanical joint assembly is in place within the pockets 22 and 24, the mechanical joint 20 will be retained in position at the side of a body joint to be treated. Adjustable posterior straps 26 and 28 and anterior straps 30 and 32 are secured to the pockets 22 and 24. The combination of an anterior and posterior strap is positioned on either side of the mechanical joint 20, and these straps cooperate to surround the limb of a user on either side of a joint to be treated. Such anterior and posterior straps insure that optimum therapeutic effectiveness is obtained from the spring tension provided by the mechanical joint 20.

The mechanical joint 20 is formed at ends of the strut members 16 and 18 which are pivoted about a pivot post 34. These pivoted ends of the strut members are bifurcated to provide an enclosure for an adjustable spring mechanism used to tension the mechanical joint 20. Thus, the first strut member 16 consists of a flat, elongate strut section 36 which, as it approaches the mechanical joint 20, is split into an upper leg 38 and a lower leg 40. The upper leg extends parallel to and is spaced from the lower leg by a bridging section 42. Similarly, the second strut member 18 includes a flat, elongate strut section 44 having a bifurcated end with a lower leg 46 which extends parallel to but is spaced from an upper leg 48 by a bridging section 50. The upper and lower legs 38 and 40 and the upper and lower legs 46 and 48 are arcuate in configuration, as illustrated by the lower legs 40 and 46 shown in FIG. 5. The upper legs 38 and 48 substantially match the lower legs in configuration.

Figure 3:
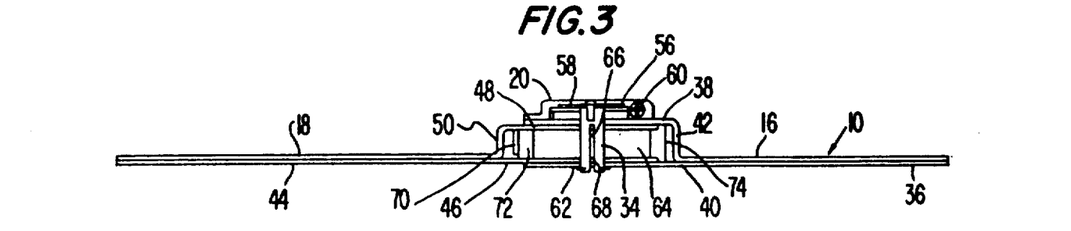
FIG. 3 is a sectional view of the strut assembly of FIG. 2.

As illustrated in FIG. 3, the legs 46 and 48 fit within the legs 38 and 40, and are mounted for pivotal movement by the pivot post 34 which extends therethrough. This pivot post creates a pivotal axis which is substantially perpendicular to the longitudinal axes 52 and 54 of the strut sections 36 and 44, respectively.

A gear housing 56 is secured to the outermost surface of the upper leg 38, and operates to enclose a gear 58 mounted upon one end of the pivot post 34. This gear meshes with an adjustment screw which is mounted for rotation in the gear housing 56. The adjustment screw has threads which engage the teeth of the gear 58 in known manner to rotate the gear and thereby rotate the pivot post 34. However, when the adjustment screw 60 is stationery, it locks the gear and the pivot post to the upper leg 38 and the lower leg 40. However, the lower leg 46 and upper leg 48 are mounted for pivotal movement about the pivot post 34.

As will be noted from FIG. 3, the pivot post extends completely through the upper legs 38 and 48 and the lower legs 40 and 46, and is held in place by a removable clip 62 which engages a groove in the pivot post. This removable clip may be formed by a spring clip, washer, or other known removable clip means, which can be removed from a groove in the pivot post 34 to facilitate disassembly of the mechanical joint 20. This permits a circular leaf-spring 64 to be mounted about the pivot post 34 between the lower and upper legs 46 and 48. One end 66 of this circular leaf-spring is secured within a central slot 68 formed in the pivot post 34, while an opposite end 70 of the leaf-spring is hooked about a post 72 which extends between the lower leg 46 and the upper leg 48. A second post 74 extends between the upper leg 38 and the lower leg 40, and this post is engaged by a step 76 formed in the periphery of the lower and upper legs 46 and 48 when the flat elongate strut sections 36 and 44 are in the extended position of FIG. 2.

Figures 5, 6, 7:
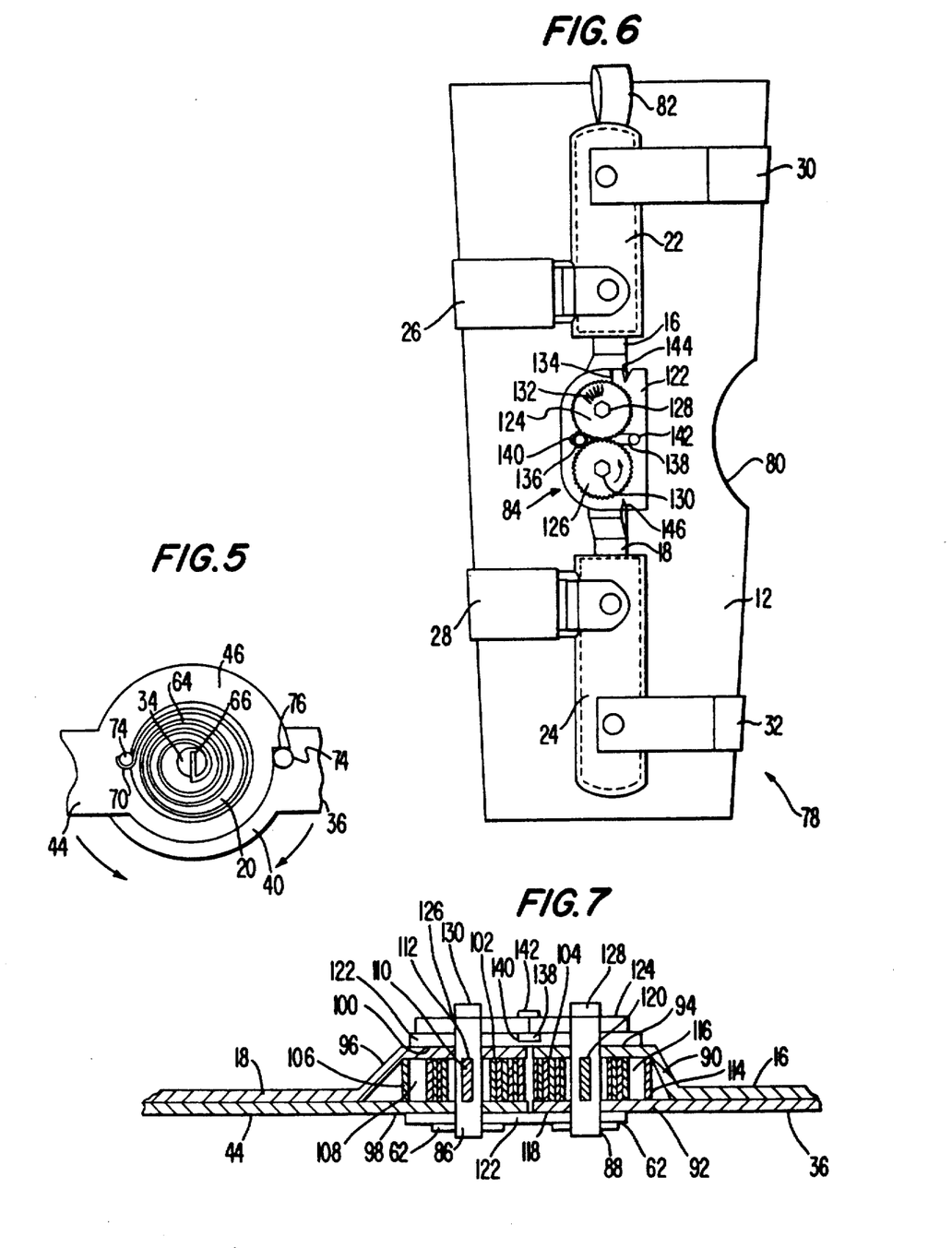
FIG. 5 is a sectional view of a biasing spring assembly used in the strut assembly of FIG. 3.
FIG. 6 is a view in side elevation of a second embodiment of the dynamic extension splint of the present invention.
FIG. 7 is a sectional view of a strut assembly for the dynamic extension splint of FIG. 6.

As will be noted from FIG. 5, when the flat elongate strut sections 36 and 44 are pivoted toward one another in the direction of the arrows in FIG. 5, the steps 76 will move away from the post 74 and the pivotal movement will be opposed by the tension of the circular leaf-spring 64. Thus, the flat, elongate strut sections move from an extended position with the steps 76 in contact with the post 74 against the bias of the spring 64 to a second closed position wherein the first and second strut members come into contact and extend from the bottom side of the mechanical joint 20 in FIG. 5. As the flat elongate strut sections 36 and 44 are pivoted back to the extended position shown in FIG. 2, the pivotal movement is aided by the bias of the spring 64. It is obvious that this bias may be adjusted by rotating the adjustment screw 60 which in turn engages and rotates the gear 58 to rotate the pivot post 34. Depending upon the direction of rotation of the pivot post, the convolutions of the spring 64 will be tightened or loosened to adjust the bias of the spring.

It is noteworthy that the flat elongate strut sections 36 and 44 are formed from aluminum or similar lightweight, bendable material. Not only does this make the dynamic extension splint 10 light and compact, but it also permits the strut sections to be bent to conform to the outer contour of the limb of a user after the splint is in place to enhance comfort. Also, since the mechanical joint 20 can be disassembled by removing the spring clip 62, the spring 64 can be reversed to reverse the direction in which the spring aids or opposes pivotal movement. This facilitates therapeutic use of the dynamic extension splint 10 to provide either flexion or extension resistance.

Figure 2:
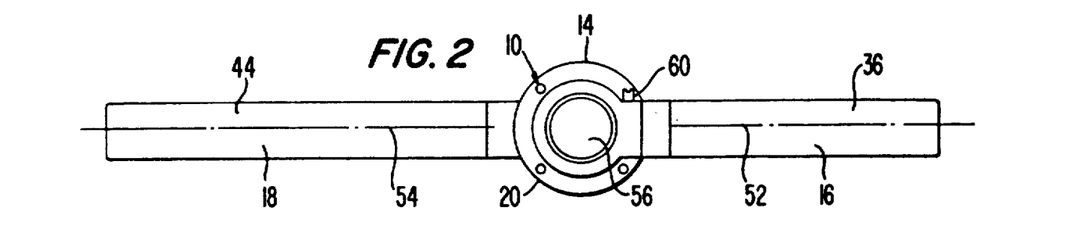
FIG. 2 is a plan view of a strut assembly for the dynamic extension splint of FIG. 1.

Referring now to FIGS. 6 and 7, a second embodiment of the dynamic extension splint of the present invention is indicated generally at 78. For purposes of description, structural elements of the dynamic extension splint 78 which are identical in structure and operation to those previously described in connection with the dynamic extension splint 10 will be designated with like reference numerals. Also, in FIG. 6, only one side of the dynamic extension splint 78 is illustrated, but it should be recognized that the first and second strut members and mechanical joint shown in FIG. 6 are provided on both sides of the suspension sleeve 12 as shown in FIG. 2.

Figure 1:
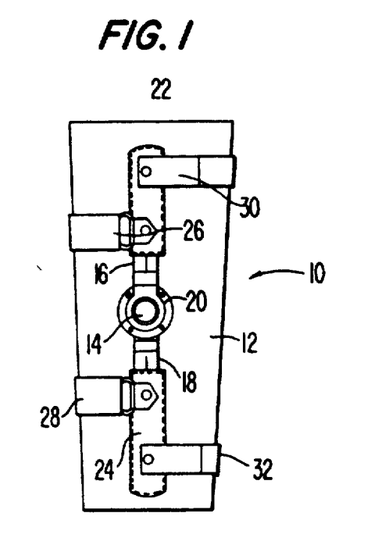
FIG. 1 is a view in side elevation of the dynamic extension splint of the present invention.

The dynamic extension splint 78 includes a suspension sleeve 12 which differs from that of FIG. 1 in that it is provided with an opening 80 to receive the patella or another portion of a body joint to be treated. The sleeve also includes pull straps on either side connected to one end of the pocket 22. These pull straps, one of which is indicated at 82, are used to pull the sleeve 12 over a limb or a body member.

The dynamic extension splint 78 differs from the splint 10 mainly in the structure of the mechanical joint, for the splint 78 includes a polycentric mechanical joint 84. This polycentric joint includes two spaced pivot pins 86 and 88 instead of the single pivot post 34 of FIG. 3. Each of these pivot pins extends through one of the bifurcated ends of the strut members 16 and 18. It will be noted that these bifurcated ends do not overlap, as illustrated in FIG. 3, but instead, are spaced apart by the pivot pins 86 and 88. Thus, as illustrated in FIG. 7, the first strut member 16 includes the flat elongate strut section 36, and a bridging section 90 which extends between a lower leg 92 and an upper leg 94. Similarly, the second strut member 18 includes the flat, elongate strut section 44 and a bridging section 96 which extends between a lower leg 98 and an upper leg 100. The bridging sections 90 and 96 space the lower legs 92 and 98 an equal distance from the upper legs 94 and 100, and circular leaf-springs 102 and 104 are mounted about the pivot pins 86 and 88 between the upper and lower legs of the first and second strut members. One end 106 of the spring 102 is hooked about a post 108 that extends between the lower leg 98 and the upper leg 100 of the second strut member 18, while an opposite end 110 of the spring 102 is secured within a slot 112 formed in the pivot pin 86. Similarly, one end 114 of the spring 104 is hooked about a post 116 which extends between the lower leg 92 and upper leg 94 of the first strut member 16, while a second end 118 of the spring is secured within a slot 120 formed in the pivot pin 88.

A housing 122 extends over the bifurcated ends of the first and second strut members 16 and 18 and encloses the polycentric mechanical joint 84. The pivot pins 86 and 88 extend outwardly on either side of the housing and on one side are clipped in place by the removable clips 62. The opposite ends of the pivot pins extend outwardly beyond the housing 122, and bear meshed gear members 124 and 126. These gear members operate to gear the pivot pins 86 and 88 together, and one gear member is are mounted on the end of each of the pivot pins to rotate therewith. Secured to the end of each pivot pin and projecting above the respective gears 124 and 126 is a tool engaging adjustment knob, with two such adjustment knobs being indicated at 128 and 130. These adjustment knobs include a plurality of flat surfaces for engagement with a wrench-type tool that is used to turn the gears 124 and 126. For example, if the tool engages the adjustment knob 130 and turns the gear 126 in the direction of the arrow in FIG. 6, then both of the pivot pins 86 and 88 are turned by an equal amount due to the mesh between the gears 126 and 128. This adjusts the bias of the springs 102 and 104 an equal amount, and the degree of tension set into the springs may be indicated by indicia 132 on the gear 124 which cooperates with a stationary indicator 134 formed on the housing 122.

To lock the gears 124 and 126 in a desired position, a small locking gear 136 is provided on the end of an elongate slide member 138 which slides in a slot 140 formed in the housing 122. The locking gear 136 has teeth which engage the teeth of the gears 124 and 126 to lock these gears in place. To unlock these gears for purposes of bias adjustment, the slide member 138 is moved to the left in FIG. 6 to disengage the gear 136. The slide member may be manipulated by means of a knob 142 provided on the end thereof opposite to the locking gear 136.

The housing 122 is formed with indentations 144 and 146 to engage the first and second strut members 16 and 18. These indentations provide stops for the strut members in the extended position shown in FIG. 6. However, the two strut members may be moved together to the left in FIG. 6 for a full 180° due to the polycentric construction of the mechanical joint 84. As the strut members pivot, the pivotal movement is transmitted by the posts 108 and 116 to the springs 102 and 104, and these springs oppose pivotal movement between an extended and a closed position in one direction while aiding pivotal movement in the opposite direction. The bias of the two springs may be adjusted equally by rotating one of the gears 124 or 126 to accomplish rotation of the opposite gear for an equal amount and therefore rotation of the pivot pins 86 and 88.

As in the case of the spring 64, the springs 102 and 104 can be reversed by removing the clips 62 and disassembling the mechanical joint 84. Thus the dynamic extension splint 78 can be configured to provide either flexion or extension resistance.

Figures 8, 9:
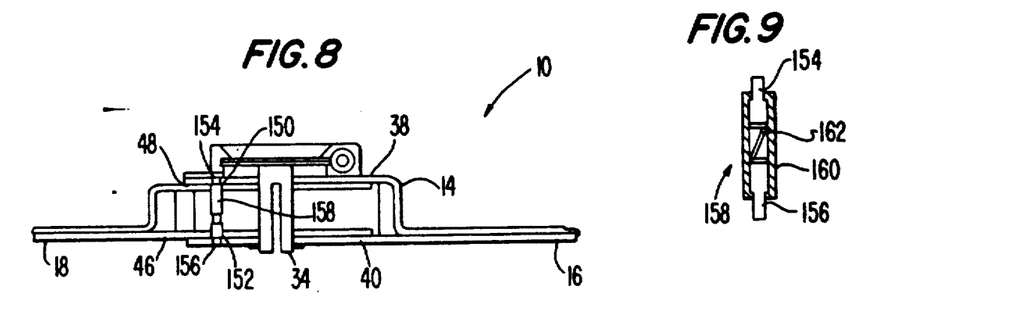
FIG. 8 is a sectional view of the strut assembly of FIG. 2 showing a range of motion stop assembly.
FIG. 9 is a sectional view of a spring loaded pin used in the range of motion stop assembly of FIG. 8.
Figure 10:
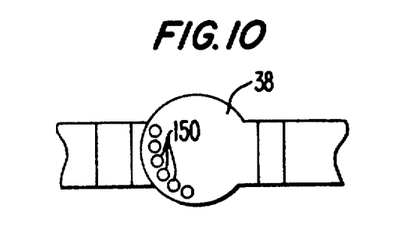
FIG. 10 is a partial plan view of the strut assembly of FIG. 8.

The dynamic extension splints 10 and 78 may be provided with an adjustable range of motion stop assembly to limit the degree of motion a body member is permitted to make around a body joint. For many types of injuries, it is beneficial to rehabilitate the body joint in stages with the degree of motion permitted by the splints being increased a free motion in a previous stage is achieved. With reference to FIGS. 8-10, the mechanical joint 14 for the dynamic extension splint 10 includes an arcuate line of spaced holes 150 and 152 formed in the legs 38 and 40 respectively. A hole 150 is aligned with a corresponding hole 152 to receive one of the spring biased pins 154 or 156 extending from opposite ends of a stop 158. The stop 158 includes a stop housing 160 that retains the pins 154 and 156 which are biased outwardly from the ends of the stop housing by a spring 162. The stop housing extends across the legs 46 and 48 so that when the pins extend into selected holes 150 and 152, the stop 158 will engage the legs 46 and 48 to limit the relative pivotal movement of the struts 16 and 18. To remove or adjust the position of the stop 158, the pins 154 and 156 are compressed into the stop housing 160 so that the stop can be disengaged from the holes 150 and 152.

Figure 11:
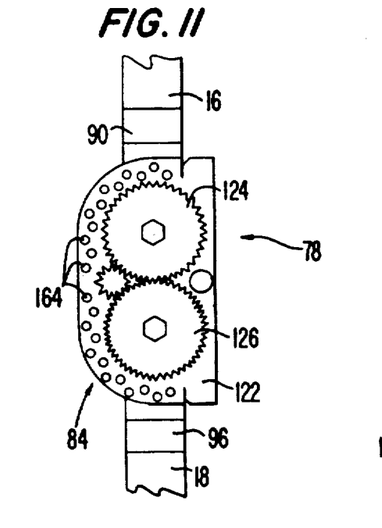
FIG. 11 is a partial plan view of a strut assembly for the dynamic extension splint of FIG. 6 showing a range of motion stop assembly.
Figure 12:
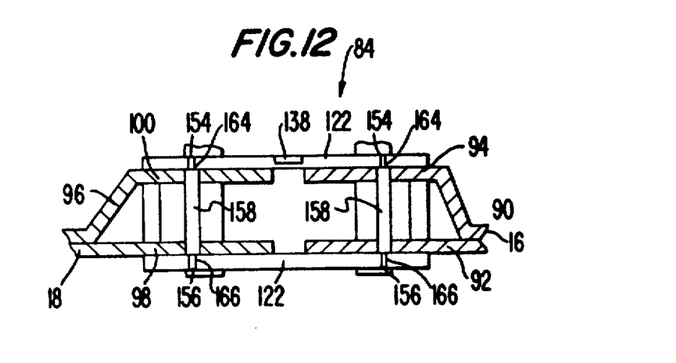
FIG. 12 is a partial sectional view of the strut assembly of FIG. 11.

The dynamic extension splint 78 shown in FIGS. 11 and 12 is also provided with a range of motion stop assembly including a plurality of arcuately arranged spaced holes 164 and 166 formed inthe upper and lower edges respectively of the housing 122. As shown in FIG. 12, which is a view of a portion of the mechanical joint 84 with the springs 102 and 104 removed for purposes of illustration, two stops 158 are positioned to span the distance between the upper and lower edges of the housing 122, with a stop extending in front of each of the bifurcated ends of the strut members 16 and 18. The spring biased pins 1654 and 156 for each stop extend into a hole 164 and 166 respectively in the housing 122. Thus, each stop limits the range of pivotal movement of a strut member 16 or 18 depending uppon where the top is positioned in the line of holes 164 or 166.

INDUSTRIAL APPLICABILITY

The dynamic extension splint of the present invention is used for the treatment of joint contractures occurring secondary to trauma, casting, or other immobilization. It is also used to restore strength and flexibility onto a body joint, by creating resistance requiring the wearer to flex the joint, thereby building strength and fluidity. The bias adjustment feature incorporated within the dynamic extension splint permits the spring bias of the splint to be varied throughout a recovery process as treatment of the joint progresses.

We claim:

1. An adjustable splint device for applying force across a body joint comprising a first elongated strut member having a longitudinal axis extending between opposed ends thereof, a second elongated strut member having a longitudinal axis extending between opposed ends thereof, joint means for connecting one end of said first and second strut members for pivotal movement about a pivot axis which is transverse to the longitudinal axes of said first and second strut members, said joint means operating to permit pivotal movement of said first and second elongated sturdy members between a first extended position where said first and second elongated strut members extend outwardly away from opposite sides of said joint means and a second closed position where said first and second elongated strut members extended outwardly in close proximity from the same side of said joint means and including at least one pivot pin mounted for rotation relative to said first and second elongated strut members about which at least one of said elongated strut members pivots, bias means mounted at said joint means and connected to provide a bias to oppose pivotal movement of said first and second elongated strut members in a first direction between said first extended position and second closed position and to aid such pivotal movement in a second direction opposite to said first direction between said first extended position and second closed position, said bias means including spring means extending around said pivot pin, sand connected between said pivot pin and at least one of said first and second elongated strut members, and bias adjustment means mounted at said joint means and operative to adjust the bias of said bias means by rotation of said pivot pin.

2. The adjustable splint device of claim 1, wherein said joint means connects one end of said first strut members for pivotal movement about a first pivot axis and connects one end of said second strut member for pivotal movement about a second pivot axis substantially parallel to but spaced from said first pivot axis.

3. The adjustable splint device of claim 2, wherein said joint means includes a first pivot pin extending through the end of said first strut member along said first pivot axis and a second pivot pin extending through the end of said second strut member along said second pivot axis, said bias means including a first spring means mounted around said first pivot pin and a second spring means mounted around said second pivot pin.

4. The adjustable splint device of claim 3, wherein said first and second pivot pins are mounted for rotation, said first spring means being connected between said first pivot pin an said first elongated strut member and said second spring means being connected between said second pivot pin and said second elongated strut member, said bias adjustment means operating to rotate said first and second pivot pins.

5. The adjustable splint device of claim 4, wherein said bias adjustment means includes gear means connected to said first and second pivot pins, said gear means operating to cause simultaneous rotation of both said first and second pivot pins.

6. The adjustable splint device of claim 5, wherein said bias adjustment means includes locking means mounted to be selectively engaged or disengaged with said gear means.

7. The adjustable splint device of claim 1, wherein said first and second strut members include an elongate, flat strut section formed of material which may be contoured to conform the strut section to various body shapes, the end of each said first and second strut members connected by said joint means for pivotal movement including a bifurcated end section, said bifurcated end section including first and second spaced, superimposed legs extending outwardly from said flat strut section.

8. The adjustable splint device of claim 7, wherein said bias means includes spring means mounted between the first and second spaced legs of the bifurcated end sections of said first and second strut members.

9. The adjustable splint device of claim 8, wherein said pivot pin extends through the bifurcated end sections of said first and second strut members, said spring means being connected between said pivot pin and at least the bifurcated end section of one of said first or second strut members.

10. An adjustable splint device for applying force across a body joint comprising a first elongated strut member having a longitudinal axis extending between opposed ends thereof, a second elongated strut member having a longitudinal axis extending between opposed ends thereof, joint means connected one end of said first and second strut members for pivotal movement about a pivot axis which is transverse to the longitudinal axes of said first and second strut members, said joint means including pivot means for mounting at least one of said first and second strut members for pivotal movement about said pivot means, said pivot means being rotatable relative to said first and second strut members, bias means mounted at said joint means and connected to provide a bias to oppose pivotal movement of said first and second strut members in a first direction and to aid said pivotal movement in a second direction opposite to said first direction, said bias means being connected between said pivot means and at least open of said first and second strut members, and bias adjustment means mounted at said joint means and operative to rotate said pivot means relative to said first and second strut members to adjust the bias of said bias means.

11. The adjustable splint device of claim 10 wherein said bias adjustment means includes gear means connected to said pivot means to cause the rotation thereof, and gear operator means connected to said gear means and operative to rotate said gear means to cause the rotation of said pivot means.

12. The adjustable splint device of claim 11 wherein said gear operator means include a rotatable adjustment screw having threads which engage said gear means to rotate said gear means up on the rotation of said adjustment screw.

13. The adjustable splint device of claim 12 wherein said bias means includes a circular leaf spring encircling said pivot means, said leaf spring having a first end connected to said pivot means and a second end connected to one of said first or second elongated strut members.

14. The adjustable splint device of claim 13 wherein said first and second elongated strut members each include an elongate flat strut section formed of material which may be contoured to conform the strut section to various body shapes, the end of each of said first and second strut members connected by said joint means for pivotal movement including a bifurcated end section connected to said strut section, said bifurcated end section including firs and second spaced, superimposed legs extending outwardly from said flat strut section, said leaf spring being mounted between the first and second spaced legs of the bifurcated end sections of said first and second strut members.

15. The adjustable sling device of claim 14 wherein the first and second legs of the bifurcated end sections of said first and second strut members are of greater width than the flat strut section connected thereto, said bifurcated end section of said first and second strut members being connected together by said pivot means with said first and second legs of the bifurcated end section of said first elongated strut member lowering the first and second legs respectively of the bifurcated end section of said second elongated strut member to form a housing for said joint means.

16. The adjustable splint device of claim 15 wherein a housing is formed on one of said first or second legs of the bifurcated end section of said fist elongated strut member, said pivot means extending through eh bifurcated end of said first and second strut members into said housing , said gear means being secured to said pivot means within said housing and said rotatable adjustment screw being mounted on said housing to extend into said housing and into engagement with said gear means.

17. The adjustable sling device of claim 15 which includes range of motion locking means to limit the extent of pivotal movement o said first and second elongated strut means, said range of motion locking means including at least one pair of aligned apertures formed in the first and second legs of said first elongated strut member and pin means adapted to be removably mounted in said aligned apertures to extend between the first and second legs of said first elongated strut member.

18. The adjustable sling device of claim 11 wherein said joint means connects one end of said fist strut member for pivotal movement about a first pivot axis and connects one end of said second strut member for pivotal movement about a second pivot axis substantially parallel to but spaced from said first pivot axis, said pivot means including a first pivot pin extending through the end of said first strut member along said fist pivot axis and a second pivot pin extending through the end of said second strut member along said second pivot axis, said first and second pivot pins being mounted for rotation relative to said fist and second strut members respectively.

19. The adjustable splint device of claim 18 wherein said bias means includes a first spring means mounted around said fist pivot pin and being connected to said first pivot pin and said first elongated strut member and a second spring means mounted around said second pivot pin and being connected to said second pivot pin and said elongated strut member, said gear means including a first gear connected to said first pivot pin and a second gear, meshed with said fist gear, connected to said second pivot pin whereby rotation of one of said fist and second pivot pins by said bias adjustment means operates to simultaneously adjust the bias of said first and second spring means.

20. The adjustable sling device of claim 19 wherein said joint means includes a joint housing having opposite open ends and an open side which open into a housing interior, the first and second pivot pins extending through said joint housing to mount the ends of said fist and second elongated strut members within said housing, said first and second gears being mounted externally of said joint housing.

21. The adjustable splint device of claim 20 wherein said first and second elongated strut members each include an elongated flat strut section formed of material which may be contoured to conform the strut section to various body shapes, each said fist and second strut members connected by said joint means for pivotal movement including a bifurcated end section connected to said strut section, said bifurcated end section including first and second spaced, superimposed legs extending outwardly from said flat strut section, said first and second spring means each including a circular leaf spring encircling said fist and second pivot pins respectively, and being positioned thereby between the superimposed legs of the bifurcated end sections for said first and seconds tut members respectively, said first pivot pin extending through the bifurcated end section of said first strut member and said second pivot pin extending through the bifurcated end section of said second strut member.

22. The adjustable splint device of claim 21 wherein the strut sections of said first and second strut members each extend outwardly from an opposite open end of said joint housing in a first extended position of said first and second strut members and pivot between said first extended position and a second closed position where the strut sections of said fist and second elongated strut members extend outwardly from the open side of said joint housing in close proximity.

23. The adjustable splint device of claim 22 wherein said bias adjustment means includes locking means mounted upon said joint housing to engage at least one of said fist or second gears to lock said first and second gears against rotation once the bias of said spring means has been adjusted.

24. The adjustable splint device of claim 23 wherein said locking means includes a locking gear slidably mounted upon said joint housing for movement into and out of meshing engagement with said first and second gears.

25. The adjustable splint device of claim 24 which includes range of motion locking means to limit the extent of pivotal movement of said first and second elongated strut means to less than the full extent of movement between said first extended position and second closed position.

26. The adjustable splint dvice of claim 25 wherein said range of motion locking means includes at least one pair of aligned apertures formed in said joint housing adjacent to and on opposite sides of the open side of said joint housing and pin means adapted to be removably mounted in said aligned apertures to extend across the open side of said joint housing.

27. The adjustable splint device of claim 10 which includes range of motion locking means mounted at said point means which is selectively operable to limit the pivotal movement of said first and second elongated strut means.

28. An adjustable splint device for applying force across a body joint in a body member, comprising a pair of elongated strut assemblies, each such strut assembly having a first elongated strut member having a longitudinal axis extending between opposed ends thereof, a second elongated strut member having a longitudinal axis extending between opposed ends thereof, joint means connecting one end of said first and second strut members for pivotal movement about a pivot axis which is transverse to the longitudinal axis of said first and second strut members, said joint means including pivot means for mounting at least one of said first and second strut members for pivotal movement about said pivot means, said pivot means a being rotatable relative to said first and second strut members, bias means mounted sat said joint means and connected to provide a bias to oppose pivotal movement of said first and second strut members in a first direction and to aid said pivotal movement in a second direction opposite to said first direction, said bias means being connected between said pivot means and at least one of said first and second strut members, bias adjustment means mounted sat said joint means and operative to rotate said pivot means relative to said first and second strut means to adjust the bias of said bias means, and strut support means mountable upon said body member for supporting said strut assemblies on opposite sides of said body joint with the joint means thereof in alignment with said body joint.

29. The adjustable splint device of claim 28 wherein said bias adjustment means for each said strut assembly includes gear means connected to said pivot means to cause the rotation thereof, and gear operator means connected to said gar mean and operative to rotate said gear means to cause the rotation of said pivot means, said strut support means operating to position said gear means and gear operator means outwardly away from contact with said body joint when said strut assemblies are mounted thereby on opposite sides of ad body joint.

30. The adjustable splint device of claim 29 wherein said strut support means removably mounts said strut assemblies to permit said strut assemblies to be removed therefrom when said strut support means is mounted on said body member.

31. The adjustable splint device of claim 30, wherein said strut support means includes first and second strap assemblies for circumventing said body member on opposite sides of said body joint, each such strap assembly including an anterior strap to extend around a first side of the body member and a posterior strap to extend around a second opposite side of the body member.

32. The adjustable splint device of claim 30 wherein said strut support means includes elastic sleeve means adapted to extend around said body member, and first and second strap assemblies for circumventing said body member on opposite sides of said body joint, said first and second strap assemblies overlying said elastic sleeve means and each including an anterior strap to extend around a first side of said body member and a posterior strap to extend around a second opposite side of the body member.

33. The adjustable splint device of claim 32 wherein said elastic sleeve means is formed of Neoprene.

34. The adjustable splint device of claim 32, wherein said strut support means includes a spaced pair of pocket means formed upon opposed sides of said strut support means, each pair of pocket means operating to removably receive the first and second elongated strut members of one of said elongated strut assemblies.

* * * * *

UNITED STATES PATENT AND TRADEMARK OFFICE
CERTIFICATE OF CORRECTION

Page 1 of 2

PATENT NO. : 5,036,837
DATED : Aug. 6, 1991
INVENTOR(S) : Mitchell et al

It is certified that error appears in the above-indentified patent and that said Letters Patent is hereby corrected as shown below:

Col. 8, Claim 1, line 11, delete "sturdy" and insert --strut-- and on line 29, delete "sand" and insert --and--.

Col. 8, Claim 7, line 5, after the word "each" insert --of--.

Col. 9, Claim 10, line 6, delete the word "connected" and insert --connecting-- and on line 19, delete "open" and insert --one--.

Col. 9, Claim 14, line 9, delete "firs" and insert --first--.

Col. 10, Claim 15, line 1, change "sling" to --splint--, on line 5, delete the word "section" and insert --sections--, and on line 8, delete "lowering" and insert --overlying--.

Col. 10, Claim 16, line 3, delete "fist" and insert --first--, on line 4, delete "eh" and insert --the--, and on line 5, delete "end" and insert --ends--.

Col. 10, Claim 17, line 1, delete "sling" and insert --splint-- and on line 3, delete "o" and insert --of--.

Col. 10, Claim 18, line 1, delete "sling" and insert --splint-- and on line 2, delete "fist" and insert --first--.

Col. 10, Claim 19, line 3, delete "fist" and insert --first--, on line 9, delete "fist" and insert --first--, and line 11, delete "fist" and insert --first--.

Col. 10, Claim 20, line 1, delete "sling" and insert --splint-- and on line 5, delete "fist" and insert --first--.

UNITED STATES PATENT AND TRADEMARK OFFICE
CERTIFICATE OF CORRECTION

PATENT NO. : 5,036,837
DATED : Aug. 6, 1991
INVENTOR(S) : Mitchell et al

It is certified that error appears in the above-indentified patent and that said Letters Patent is hereby corrected as shown below:

Col. 11, Claim 21, line 5, delete "fist" and insert --first--, on line 12, delete "fist" and insert --first--, and on line 15, delete "tut" and insert --strut--.

Col. 11, Claim 22, line 7, delete "fist" and insert --first--.

Col. 11, Claim 23, line 4, delete "fist" and insert --first--.

Col. 11, Claim 27, line 3, delete "point" and insert --joint--.

Col. 11, Claim 28, line 14, delete "a", on line 16, delete "sat" and insert --at--, and on line 22, delete "sat" and insert --at--.

Col. 12, Claim 29, line 5, delete "gar mean" and insert --gear means--, and on line 10, delete "ad" and insert --said--.

Signed and Sealed this

Fourteenth Day of March, 1995

BRUCE LEHMAN

Attest:

Attesting Officer

Commissioner of Patents and Trademarks